(12) United States Patent
Berthelemy et al.

(10) Patent No.: US 12,156,935 B2
(45) Date of Patent: Dec. 3, 2024

(54) COSMETIC AND DERMATOLOGICAL USES OF AN EXTRACT FROM THE FUNGUS *Inonotus obliquus*

(71) Applicant: BASF Beauty Care Solutions France SAS, Lyons (FR)

(72) Inventors: Nicolas Berthelemy, Essey-les-Nancy (FR); Catherine Bonnaud-Rosaye, Essey-les-Nancy (FR); Sèbastien Cadau, Lyons (FR); Christine Jeanmaire, Essey-les-Nancy (FR); Sabrina Leoty-Okombi, Lyons (FR); Philippe Moussou, Essey-les-Nancy (FR); Nicolas Pelletier, Lyons (FR)

(73) Assignee: BASF Beauty Care Solutions France SAS, Lyons (FR)

( * ) Notice: Subject to any disclaimer, the term of this patent is extended or adjusted under 35 U.S.C. 154(b) by 727 days.

(21) Appl. No.: 17/288,687

(22) PCT Filed: Oct. 23, 2019

(86) PCT No.: PCT/FR2019/052535
§ 371 (c)(1),
(2) Date: Apr. 26, 2021

(87) PCT Pub. No.: WO2020/084259
PCT Pub. Date: Apr. 30, 2020

(65) Prior Publication Data
US 2021/0393508 A1 Dec. 23, 2021

(30) Foreign Application Priority Data
Oct. 26, 2018 (FR) ..................... 1859909

(51) Int. Cl.
| | | |
|---|---|---|
| *A61K 36/00* | (2006.01) | |
| *A61K 8/9728* | (2017.01) | |
| *A61K 36/07* | (2006.01) | |
| *A61P 17/00* | (2006.01) | |
| *A61Q 17/00* | (2006.01) | |
| *A61Q 19/02* | (2006.01) | |
| *A61Q 19/08* | (2006.01) | |

(52) U.S. Cl.
CPC ............ *A61K 8/9728* (2017.08); *A61K 36/07* (2013.01); *A61P 17/00* (2018.01); *A61Q 17/00* (2013.01); *A61Q 19/02* (2013.01); *A61Q 19/08* (2013.01)

(58) Field of Classification Search
CPC .................................................. A61Q 19/08
See application file for complete search history.

(56) References Cited

FOREIGN PATENT DOCUMENTS

| | | | | |
|---|---|---|---|---|
| CN | 105535035 A | 5/2016 | | |
| CN | 106309509 A | 1/2017 | | |
| CN | 106420500 A | 2/2017 | | |
| CN | 106860310 A | * 6/2017 | ............... | A61K 8/35 |
| JP | 2006-028019 A | 2/2006 | | |
| KR | 10-2004-0102773 A | 12/2004 | | |
| KR | 20040102558 A | * 12/2004 | | |
| KR | 10-2005-0038112 A | 4/2005 | | |
| KR | 10-0863890 B1 | 10/2008 | | |
| KR | 10-2011-0101433 A | 9/2011 | | |
| WO | 2002/051828 A2 | 7/2002 | | |
| WO | 2018/115303 A1 | 6/2018 | | |

OTHER PUBLICATIONS

Seo et al., Antioxidant activity of subcritical water extracts from Chaga mushroom (*Inonotus obliquus*). Separation Science and Technology (2010), 45(2), 198-203 (Year: 2010).*
Liu et al., "Chapter 3: Blood Vessels and Nerves" 37 pages.
Tian et al., "VI. Dynamic indicators of microblood flow", 18 pages.
Wu et al., "Chapter V Clinical Acupotomy Therapy", Chinese Acupotomology, 12 pages.
"Eye Cream: Nature Republic" ID 1988406, URL: http://www.gnpd.com, 2013, 6 pages.
Mintel "Eye Serum The Saem International", ID4394489, URL: http://www.gnpd.com, 2016, 5 pages.
Mintel "Intensive Anti-Wrinkle Eye Cream" Grassroots Life, ID 1405047, URL: http://www.gnpd.com, 2010, 6 pages.
Xian et al., "State Food and Drug Administration Technical Requirements for Cosmetic Products," Product Technical Requirement, Feb. 6, 2023, 11 pages.
Xiang et al., "Practical TCM Dermatology Diagnosis and Treatment and Cosmetic Techniques," Traditional Chinese Medicine Ancient Books Publishing House, Sep. 2016, 18 pages.
International Preliminary Report on Patentability received for PCT Patent Application No. PCT/FR2019/052535, mailed on May 6, 2021, 15 pages (6 pages of English Translation and 9 pages of Original Document).
International Search Report and Written Opinion received for PCT Patent Application No. PCT/FR2019/052535, mailed on Feb. 24, 2020, 19 pages (9 pages of English Translation and 10 pages of Original Document).
The Saem. "Global Eco the Saem", Jan. 20, 2020, Retrieved from the Internet: https://www.thesaemcosmetic.com/en/page/product/detail/10746, 4 pages.

(Continued)

*Primary Examiner* — Qiuwen Mi
(74) *Attorney, Agent, or Firm* — Faegre Drinker Biddle & Reath LLP (57) ABSTRACT

The invention relates to the use of an extract of the fungus *Inonotus obliquus* for maintaining and/or increasing the cohesion of the skin tissues, for preventing the appearance of and/or for reducing shadows and/or bags in the area around the eyes, for maintaining and/or increasing the radiance and/or homogeneity of the skin complexion and/or for maintaining and/or increasing the barrier function of the skin and/or for increasing the skin microcirculation. The invention also relates to the extract of *I. obliquus* or a dermatological composition comprising same, for its use for reducing ruddiness and/or for preventing and/or reducing pathologies resulting from a reduction in the cohesion of the skin tissues, notably itching and/or couperosis.

8 Claims, 2 Drawing Sheets

(56) References Cited

OTHER PUBLICATIONS

The Saem. "The Saem CHAGA Anti-Wrinkle Eye Cream: Amazon. in: Beauty", Amazan.com, May 13, 2017, pp. 1-2, Retrieved from the Internet: https://www.amazon.in/Saem-CHAGA-Anti-Wrinkle-Eye-Cream/dp/B071F5N2MG [retrieved on Jan. 20, 2020].
Bai X., "New Technology for Food Inspection", China Metrology Press, Jan. 2010, pp. 8-9.

* cited by examiner

FIG 3 type IV collagen (A)                  (B)

FIG 4

COSMETIC AND DERMATOLOGICAL USES OF AN EXTRACT FROM THE FUNGUS *Inonotus obliquus*

CROSS-REFERENCE TO RELATED APPLICATIONS

This application is a national stage application (under 35 U.S.C. § 371) of PCT/FR2019/052535, filed Oct. 23, 2019, which claims benefit of French Application No. 1859909, filed Oct. 26, 2018, both of which are incorporated herein by reference in their entirety.

The present invention relates to the use of an extract of *Inonotus obliquus* for maintaining and/or increasing the cohesion of the skin tissues and to the applications thereof in the fields of cosmetics and dermatology.

The skin microcirculation is a system for draining cellular toxins, in addition to constituting a system for supplying cells with nutrients. This skin microcirculation is optimal when the cells, in particular endothelial and lymphatic cells, have good cohesion. Under conditions of stress or fatigue or when subjected to detrimental environmental conditions, this skin microcirculation is modified. This is reflected by a decrease in the cohesion of the endothelial and lymphatic tissues, an increase in cell permeability, and non-optimal draining of toxins and thus accumulation of toxins. The consequence is visible on facial skin. A dull complexion and alteration of the skin in the area around the eyes, the skin being particularly thin in this area, are thus noted. This may be reflected by the appearance of bags and shadows under the eyes. The cohesion notably of the endothelial cells is ensured by the type IV collagen proteins, VE-cadherin, CD31 or PECAM-1 (Platelet and Endothelial Cell Adhesion Molecule 1), which is another constituent protein of the cellular junctions of the endothelial and lymphatic cells.

Besides these manifestations, the appearance of signs on the face such as ruddiness, itching, irritation, or even couperosis, will be noted in more severe conditions.

Active ingredients which have the effect of reducing shadows and bags in the area around the eyes exist on the cosmetics market, as do active ingredients that are capable of improving the radiance of the complexion. However, the cosmetics field is in constant search for alternative and novel ingredients having, inter alia, these effects.

Surprisingly, the Applicant has found that an extract of *I. obliquus* has the capacity for reducing shadows and bags in the area around the eyes, but also for increasing the radiance and homogeneity of the skin complexion. This extract has also proven to be capable of notably reducing ruddiness and also couperosis.

The fungus *I. obliquus* is a basidiomycete fungus of the Hymenochaetaceae family known under the name chaga or clinker polypore. It is found on birch bark, in several regions worldwide, notably in Russia, Canada and Eastern Europe.

It is an edible fungus, which is moreover known for its medicinal properties, notably for treating gastrointestinal disorders, cardiovascular diseases and diabetes. Antioxidant, anti-inflammatory, antitumoral and anti-hyperglycaemiant effects are attributed thereto.

Extracts of *I. obliquus* have already been described in cosmetic compositions. Thus, patent application KR 2004/0102773 discloses a cosmetic composition comprising an extract of *I. obliquus* for its free-radical-scavenging and bleaching properties. Nothing in said patent application discloses or suggests a use of the extract according to the invention for increasing the cohesion of skin tissues or for reducing ruddiness or increasing the luminous appearance of the skin, and all the less so for reducing shadows or bags in the area around the eyes.

Patent application KR 2007/0046139 discloses a cosmetic composition containing a combination of four different fungal extracts including an extract of *I. obliquus*. However, said document does not disclose an effect of the extract of *I. obliquus* according to the invention for increasing the cohesion of skin tissues, notably for reducing ruddiness of the skin in particular, and all the less so for increasing the radiance of the complexion.

None of the documents cited previously discloses the properties of the extract of *I. obliquus* according to the invention for reducing shadows and/or bags in the area around the eyes. None of these documents describes, either, the use of an extract of *I. obliquus* alone for maintaining and/or increasing the radiance of the skin complexion.

The advantage of the extract according to the invention is that it is a starting material available in large amount, which can be produced on an industrial scale. Another advantage is that this extract has the capacity for stimulating several protein targets concomitantly, in several cell types. Finally, according to a particular embodiment, the extract according to the invention is obtained in water under subcritical conditions, the extraction process not using any organic solvent, while at the same time allowing the production of an extract rich in sparingly polar compounds, which are usually poorly extracted under conventional temperature and pressure conditions.

A first subject of the invention is thus the cosmetic use of an extract of *I. obliquus* for maintaining and/or increasing the cohesion of the skin tissues.

The expression "maintaining and/or increasing the cohesion of the skin tissues" means herein maintaining and/or increasing the cohesion of lymphatic and/or epithelial cells, and/or the cohesion of the epidermis, and/or the cohesion of the dermo-epidermal junctions. Thus, the extract of *I. obliquus* according to the invention makes it possible to prevent the appearance of and/or to reduce shadows and/or bags in the area around the eyes and/or to maintain and/or increase the radiance and/or homogeneity of the skin complexion.

A subject of the invention is moreover a cosmetic care process comprising the oral or topical administration of an extract of *I. obliquus* or of a cosmetic composition comprising same for maintaining and/or increasing the cohesion of skin tissues, in particular for preventing the appearance of and/or for reducing shadows and/or bags in the area around the eyes, and/or for maintaining and/or increasing the radiance and/or homogeneity of the skin complexion and/or for maintaining and/or increasing the barrier function and/or for maintaining and/or increasing the skin microcirculation.

A third subject of the invention relates to the extract of *I. obliquus* or a dermatological composition comprising same, for its use for preventing and/or reducing pathologies associated with a loss of cohesion of the skin tissues, notably itching and/or stinging and/or irritations and/or burning sensations and/or visible squamae, and/or for preventing and/or reducing couperosis and/or ruddiness.

A first subject thus relates to the cosmetic use of an extract of *I. obliquus* for maintaining and/or increasing the cohesion of the skin tissues.

For the purposes of the invention, the term "cosmetic use" means a non-therapeutic use, i.e. a use which does not require a therapeutic treatment and which is intended for healthy skin and/or mucous membranes, i.e. skin not presenting a dermatological pathology, in the present case skin not having any infections, scars, diseases or skin complaints such as candidiasis, impetigo, psoriasis, eczema, acne or dermatitis, or couperosis, or wounds or injuries.

The extract according to the invention is a topically acceptable active extract. The term "topically acceptable" means herein a non-toxic extract that is suitable for topical application, which is non-irritant to the skin and/or mucous membranes, which does not induce an allergic response, and which is not chemically unstable.

The use of the extract according to the invention may be by oral or topical administration. Advantageously, the extract is applied topically. The term "topically" means the direct local application and/or spraying of the extract onto the surface of the skin and/or mucous membranes.

The term "mucous membrane" means the vaginal mucous membrane, the urogenital mucous membrane, the anal mucous membrane, the nasal mucous membrane, the oral mucous membrane, the ocular mucous membrane, the labial and/or gingival mucous membrane, preferentially the labial mucous membrane.

The extract according to the invention may be applied topically to all or part of the face and/or the body, the scalp and/or the mucous membranes, chosen from the legs, the hands, the thighs, the stomach, the neckline, the neck, the arms, the torso, the back, the face, notably the area around the eyes, advantageously the neckline and/or the face and notably the area around the eyes, even more advantageously the area around the eyes. For the purposes of the invention, the area around the eyes includes the eyelids.

The expression "maintaining and/or increasing the cohesion of the skin tissues" means maintaining and/or increasing the cohesion of endothelial and/or lymphatic cells, by maintaining and/or increasing the gene and/or protein expression of the adhesion markers present in the cells chosen from VE-cadherin and/or collagen, and/or by maintaining and/or re-establishing the structure of endothelial cells subjected to a stress.

Increasing the cohesion of endothelial and/or lymphatic cells makes it possible to prevent the appearance of and/or to reduce shadows and/or bags in the area around the eyes.

The expression "reducing shadows and/or bags" thus means increasing the protein and/or gene expression of VE-cadherin and/or collagen, it being understood that increasing the gene expression is defined as increasing the expression of the corresponding mRNAs.

Thus, for the purposes of the invention, the expression "increasing the expression of VE-cadherin" means increasing its gene and/or protein expression by at least 5% in the presence of the extract of *I. obliquus*, preferentially by at least 10%, more preferentially by at least 15% in comparison with the level of expression detected in the absence of the extract.

In an advantageous embodiment of the invention, it is a matter of increasing the protein expression of VE-cadherin, advantageously measured in endothelial cells, more advantageously in the presence of the extract of *I. obliquus* prepared according to Example 1d) or according to Example 1k), very advantageously measured by immunohistochemistry and detected by confocal microscopy under the conditions described in Example 2.

The expression "re-establishing the structure of endothelial cells subjected to a stress" means re-establishing, in the presence of the extract of *I. obliquus* according to the invention, a structure of endothelial cells which has sagged and collapsed when subjected to a stress, advantageously in the presence of TNF-α (Tumour Necrosis Factor-α). In an advantageous embodiment of the invention, the re-establishment of the structure of said cells will be evaluated by labelling the protein CD31 (or PECAM-1) in a model of reconstructed dermis in the presence of the extract of *I. obliquus* according to the invention, in comparison with said model stressed in the presence of TNF-α (control), more preferentially in the presence of the extract of *I. obliquus* prepared according to Example 1d) or according to Example 1k). Very advantageously, the re-establishment of the structure of said cells will be evaluated by immunohistochemistry and detected by confocal microscopy under the conditions described in Example 3.

Finally, the expression "increasing the expression of collagen" means increasing the gene and/or protein expression of collagen IV. The increase of this expression may be measured in several cell types chosen from keratinocytes and/or endothelial cells and/or fibroblasts.

The extract of *I. obliquus* will be in an amount that is effective for increasing the gene and/or protein expression of type IV collagen when the increase will be at least 5%, preferentially at least 15%, more preferentially at least 20% and very preferentially at least 40% in endothelial cells, in the presence of the extract of *I. obliquus*, in comparison with the level of expression detected without any extract. Advantageously, it will be an increase in the protein expression of type IV collagen, more advantageously measured in the presence of the extract as prepared under the conditions described in Example 1d) or according to Example 1k). This increase will preferentially be measured by immunohistochemistry under the conditions of Example 4c).

The extract of *I. obliquus* according to the invention may thus be used for protecting and/or comforting fragile and/or thin and/or sensitive skin and/or mucous membranes. The extract is useful for maintaining and/or increasing the skin microcirculation (systemic and pulmonary), it being understood that, for the purposes of the invention, the skin microcirculation does not include the blood circulation.

For the purposes of the present invention, the expression "sensitive skin or mucous membranes" means skin or mucous membranes which no longer tolerate or only very sparingly tolerate their environment on account of external factors such as the wind, pollution, cold and heat.

For the purposes of the invention, sensitive skin and/or mucous membranes are not atopic skin and/or mucous membranes. Thus, in an advantageous embodiment of the invention, the extract of *I. obliquus* or the cosmetic composition comprising same is used for treating sensitive skin and/or mucous membranes, with the exception of atopic skin and/or mucous membranes, it being understood that the term "atopic skin or mucous membranes" means herein skin or mucous membranes which are severely dehydrated and which lead to atopic dermatitis or dermatoses termed as "atopic" by a dermatologist.

Moreover, the expression "maintaining and/or increasing the cohesion of the skin tissues" means maintaining and/or increasing the cohesion of the dermo-epidermal junctions. The expression "maintaining and/or increasing the cohesion of the dermo-epidermal junctions" means maintaining and/or increasing the gene and/or protein expression of HSP70 (Heat Shock Protein 70) and/or of collagen, preferentially of type IV collagen, in keratinocytes and/or fibroblasts.

Thus, the extract of *I. obliquus* will be in an amount that is effective for increasing the gene and/or protein expression of type IV collagen when the increase will be at least 50%, preferentially at least 80%, more preferentially at least 94% and very preferentially at least 130% in keratinocytes, in the presence of the extract of *I. obliquus* according to the invention, in comparison with the level of expression detected without any extract according to the invention. Advantageously, it will be an increase in the protein expression of type IV collagen, more advantageously measured in the presence of the extract as prepared under the conditions described in Example 1d) or according to Example 1k). This increase will preferentially be measured by immunohistochemistry under the conditions of Example 4a).

The expression "increasing HSP70 expression" means a gene and/or protein increase of at least 10%, preferentially of at least 20%, more preferentially of at least 30% of the HSP70 expression in the presence of the extract of *I. obliquus* according to the invention, in comparison with the level of expression detected without any extract. In an advantageous embodiment, it will be an increase in the protein expression of HSP70, more preferentially measured in dermal fibroblasts. Preferentially, the protein expression will be measured by immunohistochemistry and the proteins will be detected by Western blotting, under the conditions of Example 5.

Increasing the cohesion of the dermo-epidermal junctions makes it possible to increase the radiance and/or homogeneity of the skin complexion. Thus, one subject of the invention is the use of the extract of *I. obliquus* for maintaining and/or increasing the radiance and/or homogeneity of the skin complexion.

For the purposes of the present invention, the expression "increasing the radiance of the complexion" means increasing the luminous appearance of the skin and/or improving the radiance and/or reducing the dull and/or sallow complexion of the skin. The radiance of the skin complexion may be measured by chromametry or by image analysis. This latter in vivo measurement method consists in taking high-resolution photographs in crossed polarized configuration of volunteers' faces taken at 45° before and after application of the test product. On the basis of these digital photographs, image analysis enables the extracting and quantifying of specific parameters (for example: L*, a*, b*, C, h°) related to the colour, the brightness, the homogeneity, and the texture of the skin.

Thus, in a particular embodiment, the extract according to the invention is in an amount that is effective for "increasing the radiance of the complexion" when the increase in the luminous appearance of the skin is at least 0.5% in the presence of the extract of *I. obliquus* according to the invention. In a preferential embodiment of the invention, it is an increase in the parameter L* measured after 28 days of application of a formulation comprising the extract of *I. obliquus* to the face of a population of 33 women, in comparison with the application under identical conditions of said formulation not comprising the extract, and under the conditions described in Example 6 (Table 4). More preferentially, it will be the formulation described in Example 9), comprising the extract of *I. obliquus* as prepared according to Example 1c).

In an advantageous embodiment of the invention, the extract of *I. obliquus* is not used in combination with an extract of the fruit of *Lycium chinense* for its use for maintaining and/or increasing the radiance and/or homogeneity of the complexion, notably in a cosmetic or dermatological composition intended for maintaining and/or increasing the radiance and/or the homogeneity of the complexion. More preferentially, the extract of *I. obliquus* according to the invention is not used in combination with an extract of the fruit of *Lycium chinense*, in particular in a cosmetic or dermatological composition according to the invention.

Finally, the expression "maintaining and/or increasing the cohesion of the skin tissues" means maintaining and/or increasing the cohesion of the epidermis.

The expression "maintaining and/or increasing the cohesion of the epidermis" means maintaining and/or increasing the gene and/or protein expression of involucrin and/or maintaining and/or increasing the gene and/or protein expression of integrin-β-1 and/or of occludin and/or of claudin-1. The extract of *I. obliquus* according to the invention will thus be in an amount that is effective for increasing the cohesion of the epidermis when the increase in the gene and/or protein expression of involucrin, preferentially the protein expression, will be at least 50% in the presence of the extract of *I. obliquus*, advantageously 100%, more advantageously 200% and very advantageously 400%, in comparison with the level of expression of said protein detected without any extract. In an advantageous embodiment, the increase in the protein expression of involucrin will be measured in the presence of the extract of *I. obliquus* prepared according to Example 1d) or according to Example 1k), in "normal" keratinocytes (obtained from a tissue not presenting any pathologies), and more advantageously, the increase in the protein expression will be detected by ELISA under the conditions described in Example 7.

Increasing the expression of involucrin moreover makes it possible to improve the barrier function of the skin. The extract of *I. obliquus* may thus be used for maintaining and/or increasing the barrier function of the skin. For the purposes of the present invention, the expression "maintaining and/or increasing the barrier function" means maintaining and/or increasing the cohesion of the cornified layer by differentiation of the keratinocytes into corneocytes, and thus the homeostasis of the epidermis and the capacities for maintaining the moisturization of the epidermis.

The expression "maintaining and/or increasing the cohesion of the epidermis" moreover means maintaining and/or increasing the gene and/or protein expression of integrin-β-1 and/or of occludin and/or of claudin-1.

Thus, the extract of *I. obliquus* is in an amount that is effective for increasing the gene and/or protein expression of integrin-β-1, preferentially the protein expression, when this increase is at least 50%, advantageously at least 70% and more advantageously at least 85% in the presence of the extract of *I. obliquus*, in comparison with the level of expression, preferentially of protein expression, of integrin-β-1 detected without any extract.

The expression "maintaining and/or increasing the gene and/or protein expression of occludin" also means maintenance and/or an increase, preferentially a protein increase, of at least 20%, preferentially at least 30% and more preferentially at least 50% in the presence of the extract of *I. obliquus*, in comparison with the level of expression, preferentially of protein expression, of occludin detected without any extract.

The expression "maintaining and/or increasing the gene and/or protein expression of claudin-1" means a gene and/or protein, advantageously a protein, maintenance and/or increase of at least 10%, advantageously of at least 20%, in the protein expression of claudin-1 in the presence of the extract of *I. obliquus*, in comparison with the level of expression, preferentially of protein expression, of claudin-1 detected without any extract.

In an advantageous embodiment, each of the increases in the protein expression of claudin-1, of occludin and of integrin-β-1 will be measured in the presence of the extract of *I. obliquus* prepared according to Example 1d) or according to Example 1k), in "normal" keratinocytes, i.e. keratinocytes obtained from a tissue not presenting any pathologies). More advantageously, this increase in protein expression will be detected by immunolabelling, under the conditions described in Example 8.

The extract of *I. obliquus* may be extracted from all of the fungus or from one or more parts of the fungus, notably chosen from the mycelium or the *sclerotium* and mixtures thereof. The extract according to the invention is preferentially an extract of *I. obliquus sclerotium*.

The extract of *I. obliquus* may be obtained via any extraction method known to those skilled in the art, chosen from hot decoction, milling including ultrasonic milling, using a mixer, maceration, extraction in water under subcritical conditions or extraction using a solvent. Advantageously, the extraction will be performed in water under subcritical conditions.

The term extraction under "subcritical conditions" means extraction in the presence of water, under temperature conditions of greater than 100° C. and pressure conditions of less than 22.1 MPa (221 bar), such that the water remains in the liquid state but has a viscosity and a surface tension lower than that of water at room temperature, increasing its dielectric constant.

Thus, the extraction pressure will be between 10 MPa (100 bar) and 25 MPa (250 bar), preferentially between 15 and 22.1 MPa (150 and 221 bar).

The extraction may be performed using dry or fresh matter, advantageously dry matter, in an amount of from 0.1% to 20% by weight, advantageously from 1% to 10%, very advantageously from 5% to 10%, even more advantageously of 10% by weight relative to the total weight of the matter and of the extraction solvent.

The extraction may be performed at a temperature ranging from 4° C. to 300° C., including room temperature, that is to say a temperature of 20° C. In a preferential embodiment of the invention, the extraction will be performed at a temperature of from 60° C. to 90° C., preferentially from 70° C. to 85° C., more preferentially at a temperature of 80° C.

In one alternative embodiment of the invention, the extraction will be performed at a temperature of from 4° C. to 25° C., more preferentially from 4° C. to 20° C., more advantageously at room temperature, that is to say at 20° C.

In yet another alternative embodiment of the invention, the extraction will be performed in water under subcritical conditions, at a temperature ranging from 100° C. to 300° C., advantageously from 120° C. to 250° C., more advantageously between 140° C. and 200° C. The extraction may be performed at a single given temperature or at successive increasing temperatures. In one advantageous embodiment of the invention, the extraction will be performed at a single temperature of 160° C. In an alternative embodiment, it will be performed according to a gradient of three increasing temperatures between 100° C. and 200° C., such as 120° C., 140° C. then 160° C., or 110° C., 130° C. then 150° C., or else 120° C., 145° C. then 170° C.

The extraction may be performed for a period of from a few seconds to 24 hours, preferentially from 1 minute to 12 hours, more preferentially for a period of from 5 minutes to 5 hours, and more advantageously for a period of from 15 minutes to 2 hours.

The solvent may be chosen from water, or a solvent mixture, preferably a polar protic solvent, and advantageously in water, an alcohol, a glycol, a polyol, a water/alcohol, water/glycol or water/polyol mixture (such as water mixed with ethanol, glycerol and/or butylene glycol and/or other glycols such as xylitol and/or propanediol, etc.), from 99/1 to 1/99 (w/w), advantageously in water as sole solvent.

In particular, the extract is obtained by aqueous extraction. For the purposes of the present invention, the expression "extract obtained by aqueous extraction" means any extract obtained by extraction with an aqueous solution containing more than 60% by weight, advantageously at least 70% by weight, in particular at least 80% by weight, more particularly at least 90% by weight, particularly at least 95% by weight, of water relative to the total weight of the aqueous solution, even more advantageously not containing glycol and in particular not containing alcohol, more particularly only containing water.

In one alternative embodiment, the extract is obtained by extraction in a mixture of propanediol and water in the respective proportion (80:20; v/v).

In another alternative embodiment of the invention, the extraction may be performed in the presence of a nonionic surfactant, preferentially chosen from lauryl glucoside sold under the name Plantacare® 1200UP by BASF or else caprylyl/capryl glucoside (Plantacare® 810 UP), preferentially caprylyl/capryl glucoside (Plantacare® 810 UP). The weight concentration of the nonionic surfactant may be between 0.5% and 5%, advantageously between 0.5% and 1%; more advantageously, it will be 1% by weight relative to the total weight of the extract.

In a particularly advantageous embodiment of the invention, the extract will be obtained by extraction in water under subcritical conditions. In this case, said extract will be different, in terms of compounds present, from the aqueous extracts obtained under conventional extraction conditions, including aqueous extracts obtained in water at temperatures ranging up to 80° C.

In a first embodiment of the invention, the extract of *I. obliquus* may be obtained by dissolution in water as sole solvent of an amount of 10% by weight of *I. obliquus* mycelium or *sclerotium* relative to the total amount of fungus and of solvent, and maceration with stirring for a period of 1 hour, at a temperature of 80° C. The extract thus obtained will be decanted and centrifuged and the supernatant will be filtered (0.45 μm) under the conditions described in Example 1a) or in Example 1h). The extract is a liquid extract termed an aqueous extract, obtained at elevated temperature as defined above.

In another embodiment, the extract of *I. obliquus* will be obtained from a ground and dried amount of 10% by weight of mycelium or *sclerotium* of the fungus relative to the total amount of fungus and of solvent, dissolved in an ethanol/water mixture (70/30; v/v). The maceration performed will take place for a period of 1 hour at a temperature of 60° C. The extract obtained is decanted and centrifuged and the supernatant obtained is filtered (0.45 μm). The ethanol is evaporated off and the extract is filtered again (0.45 μm), under the conditions described in Example 1b) or in Example 1i).

In yet another embodiment of the invention, the extraction will be performed in water under subcritical conditions using a ground and dried amount of 10% by weight of mycelium or *sclerotium* of the fungus. The extraction is performed at a temperature of 160° C.

The extract is concentrated and filtered (0.45 μm) and is in the form of an aqueous solution, under the conditions presented in Example 1c) or in Example 1j).

Another alternative embodiment of the invention will consist in grinding and drying the extract obtained under the conditions of Example 1c) or of Example 1j) to obtain an extract in powder form, under the conditions described in Example 1d) or in Example 1k).

In a final embodiment, the extract obtained under the conditions described in Example 1d) or in E example 1k) above will be dissolved in a solution containing 80% by weight of glycerol, under the conditions of Example 1e) or of Example 1l).

Additional decolourizing and/or deodourizing steps may be performed on the extract at any stage of the extraction and according to the techniques known to those skilled in the art. In particular, the extract may be decolourized with active charcoal. The extract may also be lyophilized.

The extract according to the invention may be used alone or included in a cosmetic or dermatological composition. If the extract is used alone as a cosmetic active ingredient, it is advantageously dissolved in an aqueous solution comprising glycerol, advantageously present at a concentration of from 60% to 90%, more advantageously from 70% to 85%, very advantageously at a concentration of 80% by weight relative to the total weight of the water-glycerol solution comprising the extract.

In one alternative embodiment of the invention, the extract will be dissolved and/or diluted in a solvent, notably a polar solvent, such as water, an alcohol, a polyol, a glycol, such as pentylene glycol and/or butylene glycol and/or hexylene glycol and/or caprylyl glycol, or a mixture thereof, preferentially a water-glycol mixture, more preferentially containing a glycol chosen from hexylene glycol, caprylyl glycol and mixtures thereof. Advantageously, the extract obtained is diluted and/or soluble in an aqueous solution containing hexylene glycol, in particular containing between 0.1% and 10% by weight of hexylene glycol, preferentially between 0.5% and 5% by weight of hexylene glycol, relative to the total weight of the cosmetic ingredient. Advantageously, the extract obtained is diluted and/or soluble in an aqueous solution containing caprylyl glycol, in particular containing between 0.01% and 5% by weight of caprylyl glycol, preferentially between 0.1% and 1% by weight of caprylyl glycol, relative to the total weight of the aqueous solution comprising the extract.

Alternatively, the extract may be included in a cosmetic composition comprising at least one cosmetically acceptable excipient. The term "cosmetically acceptable excipient" means a cosmetic excipient that is non-irritant to the skin, which does not induce an allergic response and which is chemically stable.

A subject of the present invention is thus the use of an extract of *I. obliquus* in a cosmetic composition comprising at least one cosmetically acceptable excipient for maintaining and/or increasing the cohesion of skin tissues, in particular for preventing the appearance of and/or for reducing shadows and/or bags in the area around the eyes, and/or for maintaining and/or increasing the radiance and/or homogeneity of the skin complexion and/or for maintaining and/or increasing the skin microcirculation and/or for maintaining and/or increasing the barrier function of the skin.

In an advantageous embodiment of the invention, the extract will be present in the cosmetic composition in a concentration of between 0.0001% and 20% by weight, preferentially between 0.001% and 5% by weight and more preferentially between 0.01% and 3% by weight relative to the total weight of the composition.

Advantageously, the cosmetic composition will be applied to all or part of the face and/or the body, the scalp and/or mucous membranes, chosen from the legs, the hands, the thighs, the stomach, the neckline, the neck, the arms, the torso, the back, the face, notably the area around the eyes, advantageously the neckline and/or the face and notably the area around the eyes, even more advantageously the area around the eyes. Advantageously, the cosmetic composition may be used for protecting and/or comforting thin and/or fragile skin and/or mucous membranes, notably of the elderly or of babies.

The excipient(s) may be chosen from surfactants and/or emulsifiers, preserving agents, buffers, chelating agents, denaturing agents, opacifiers, pH modifiers, reducing agents, stabilizers, thickeners, gelling agents, film-forming polymers, fillers, mattifying agents, gloss agents, pigments, colorants, fragrances, and mixtures thereof. The CTFA (Cosmetic Ingredient Handbook, Second Edition (1992)) describes various cosmetic excipients suitable for use in the present invention.

Advantageously, the excipient(s) are chosen from the group comprising polyglycerols, esters, cellulose polymers and derivatives, lanolin derivatives, phospholipids, lactoferrins, lactoperoxidases, sucrose-based stabilizers, vitamin E and derivatives thereof, xanthan gum, natural and synthetic waxes, plant oils, triglycerides, unsaponifiable matter, phytosterols, silicones, protein hydrolyzates, betaines, amine oxides, plant extracts, sucrose esters, titanium dioxides, glycines, and parabens, and more preferably from the group consisting of steareth-2, steareth-21, glycol-15 stearyl ether, cetearyl alcohol, phenoxyethanol, methylparaben, ethylparaben, propylparaben, butylparaben, butylene glycol, caprylyl glycol, natural tocopherols, glycerol, dihydroxycetyl sodium phosphate, isopropyl hydroxycetyl ether, glycol stearate, triisononanoin, octyl cocoate, polyacrylamide, isoparaffin, laureth-7, a carbomer, propylene glycol, hexylene glycol, glycerol, bisabolol, a dimethicone, sodium hydroxide, PEG-30 dipolyhydroxystearate, caprylic/capric triglycerides, cetearyl octanoate, dibutyl adipate, grape seed oil, jojoba oil, magnesium sulfate, EDTA, a cyclomethicone, xanthan gum, citric acid, sodium lauryl sulfate, mineral waxes and oils, isostearyl isostearate, propylene glycol dipelargonate, propylene glycol isostearate, PEG 8, beeswax, glycerides from hydrogenated palm kernel oil, lanolin oil, sesame oil, cetyl lactate, lanolin alcohol, castor oil, titanium dioxide, lactose, sucrose, low density polyethylene, an isotonic saline solution, and mixtures thereof.

The cosmetic composition may be chosen from an aqueous or oily solution, a cream or an aqueous gel or an oily gel, notably a shower gel, a milk, an emulsion, a microemulsion or a nanoemulsion, which is notably oil-in-water or water-in-oil or multiple or silicone-based, a mask, a serum, a lotion, a liquid soap, an ointment, a foam, a patch, an anhydrous product, which is preferably liquid, pasty or solid, for example in the form of makeup powders, a wand or a stick, notably in the form of a lipstick. Advantageously, it will be a cream or a serum.

The cosmetic composition may also comprise active ingredients for reinforcing the barrier function of the skin and/or the mucous membranes, inducing a complementary or synergistic effect with the extract according to the invention, chosen from those which reinforce the barrier function and decrease the transepidermal water losses and/or those which increase the water content of the skin and/or of the mucous membranes and/or stimulate aquaporin synthesis in order to improve the circulation of water in the cells. Mention will be made of serine, urea and its derivatives, products such as microspheres of marine collagen and of chondroitin sulfate as a glycosaminoglycan, a formulation comprising a hyaluronic acid salt, urea, trehalose, glyceryl triacetate and Polyquaternium-51 sold, respectively, under the names Marine Filling Spheres™ and Advanced Moisturizing Complex™; hyaluronic acid microspheres sold under the name Hyaluronic Filling Spheres™; an extract of red alga or a mixture of acacia polysaccharide, alginate and serine sold, respectively, under the names Osmogelline™ and Micropatch™ Serine; or a combination of pullulan, of hyaluronic acid or a salt or derivative thereof and of alginic acid, or a salt or derivative thereof, sold under the name PatcH20™. Other compounds may be used, such as alkylcelluloses, lecithins, sphingoid-based compounds, ceramides, phospholipids, cholesterol and its derivatives, glycosphingolipids, phytosterols (stigmasterol and β-sitosterol, campesterol), essential fatty acids, 1,2-diacylglycerol, 4-chromanone, pentacyclic triterpenes, such as ursolic acid, petroleum jelly, lanolin, sugars, in particular trehalose and its derivatives, rhamnose, fructose, maltose, lactose, erythritol, mannitol, D-xylose and glucose, adenosine and its derivatives, sorbitol, polyhydric alcohols, which are advantageously $C_2$-$C_6$, and more advantageously $C_3$-$C_6$, such as glycerol, propylene glycol, 1,3-butylene glycol, dipropylene glycol, diglycerol, polyglycerol and a mixture thereof, glycerol and its derivatives, glyceryl polyacrylate, sodium lactate, pentanediol, serine, lactic acids, AHAs, BHAs, sodium pidolate, xylitol, sodium lactate, ectoin and its derivatives, chitosan and its derivatives, collagen, plankton, steroid derivatives (including DHEA, its 7-oxidized and/or 17-alkylated derivatives and sapogenins), methyl dihydrojasmonate, vitamin D and its derivatives, an extract of *Malva sylvestris* or an extract of *Centella asiatica*, acrylic acid homopolymers, β-glucan and in particular sodium carboxymethyl β-glucan, a C-glycoside derivative such as those described in patent application WO 02/051828, a musk rose oil, an extract of the microalga *Prophyridium cruentum* enriched with zinc, sold by Vincience under the name Algualane Zinc™, arginine, acetyl hexapeptide sold by Lipotech under the name Diffuporine™, the hydrolysate of *Viola tricolor* sold by Silab under the name Aquaphyline™, or a polysaccharide extracted from *Cassia angustifolia* seeds, sold under the name Hyalurosmooth™ by the Applicant, a fermented hydrolysate of *Saccharomyces cerevisiae* sold under the name Relipidium™, or else one or more of the compounds of natural moisturizing factor or a natural extract of honey sold by the Applicant under the name Melhydran™.

Other types of active agents may be present in the composition, such as anti-ageing ingredients and/or bleaching active agents, antipollution ingredients and/or ingredients which promote the radiance of the complexion.

These agents may be, for example, a leaf extract of *Cassia alata* sold under the name DN-Age™ and/or an extract of lychees sold under the name Litchiderm™ as antioxidant active agents, a combination of an extract of *Salvia miltiorhizza* and of niacinamide, sold under the name CollRepair™ as a deglycating agent, an anti-wrinkle extract of chicory, sold under the name Lox-Age™, an extract of *Achillea millefolium* sold under the name Neurobiox™, an extract of *Polygonum bistorta* sold under the name Perlaura™, an extract of galanga sold under the name Hyalufix™, an extract of corn sold under the name Deliner™ or an extract of *Voandzeia subterranea* sold under the name Epigenist™ by the Applicant or else active agents which promote the firmness of the skin, such as a synthetic tetrapeptide sold under the name Dermican™ an extract of *Hibiscus abelmoschus* sold under the name Linefactor™, a purified extract of pea sold under the name Proteasyl™, an extract of *Manilkara multinervis* sold under the name Elestan™ or a pulp extract of Argan sold under the name Argassential™ by the Applicant. An extract of the *Origanum majorana* plant sold under the name Dermagenist™ and/or an extract of *Khaya senegalensis* sold under the name Collalift®18 may also be added to the cosmetic composition.

As antipollution agents and/or agents which promote the radiance of the skin, mention will be made an extract of argan oil sold under the name Arganyl™ and a seed extract of *Moringa oleifera* sold under the name Purisoft™ by the Applicant.

Advantageously, it will not be an extract of the fruit of *Lycium chinense*.

Another subject of the present invention relates to a cosmetic care process comprising the topical or oral administration, preferentially the topical application, of an extract of *I. obliquus* or of a cosmetic composition comprising same, for maintaining and/or increasing the cohesion of skin tissues, in particular for maintaining and/or increasing the cohesion of endothelial and/or lymphatic cells, and/or the cohesion of the epidermis, and/or the cohesion of the dermo-epidermal junctions.

Thus, said process makes it possible to prevent the appearance of and/or to reduce shadows and/or bags in the area around the eyes. Moreover, the cosmetic care process makes it possible to maintain and/or increase the radiance and/or homogeneity of the skin complexion. In this case, the extract of *I. obliquus* is not used in combination with an extract of the fruit of *Lycium chinense*. Said process also makes it possible to maintain and/or increase the barrier function of the skin and/or the skin microcirculation.

In one embodiment of the invention, the process consists of the topical application of the extract according to the invention or of the cosmetic composition comprising same to all or part of the face, the scalp and/or the mucous membranes and/or the body chosen from the legs, the hands, the thighs, the stomach, the neckline, the neck, the arms, the torso, the back, the face, notably the area around the eyes, advantageously the neckline and/or the face and notably the area around the eyes, even more advantageously the area around the eyes.

A final subject relates to the extract of *I. obliquus* or a dermatological composition comprising same for its use for preventing and/or reducing ruddiness (said extract not being used in combination with an extract of the fruit of *Lycium chinense*) and/or pathologies resulting from a decrease in skin tissue cohesion, in particular itching and/or stinging and/or irritations and/or burning sensations and/or visible squamae and/or couperosis, advantageously by increasing the cohesion of the vascular structures and/or of the epidermis.

The extract of *I. obliquus* or the dermatological composition comprising same may thus be used for treating intolerant and/or reactive skin and/or mucous membranes.

Intolerant and/or reactive skin or mucous membranes are skin or mucous membranes presenting with itching, stinging, irritations, subjective burning sensations, visible squamae and/or ruddiness, but are not atopic skin or mucous membranes as defined previously.

In one advantageous embodiment of the invention, the extract of *I. obliquus* or the dermatological composition comprising same will be applied topically to all or part of the face and/or the scalp and/or the mucous membranes and/or the body chosen from the legs, the hands, the thighs, the stomach, the neckline, the neck, the arms, the torso, the back, the face, notably the area around the eyes, advantageously the neckline and/or the face and notably the area around the eyes.

In a particularly advantageous embodiment of the invention, the extract of *I. obliquus* will be in an amount that is effective for "reducing ruddiness" when the decrease in ruddiness is at least 0.5%, preferentially at least 1% after 7 or 28 days of application to the face of a human population of 33 women of a formulation comprising the extract of *I. obliquus*, in comparison with a control corresponding to the same formulation without any extract.

The decrease in ruddiness may be measured in vivo by chromametry or image analysis. Thus, evaluation of the colour of the skin, notably of the face, may be performed by measuring the parameter a*.

In a preferential embodiment of the invention, it is a decrease in the parameter a* measured on faces presenting with ruddiness, more preferentially after application of the formulation as described in Example 9) comprising the extract of *I. obliquus* prepared according to Example 1c), under the conditions of Example 6 (Table 4). Advantageously, the extract of *I. obliquus* used for preventing and/or reducing ruddiness is not used in combination with an extract of the fruit of *Lycium chinense*. More advantageously, said extract is obtained in water under subcritical conditions. Alternatively, the dermatological composition comprising the extract of *I. obliquus* according to the invention used for preventing and/or reducing ruddiness does not comprise any extract of the fruit of *L. chinense*.

In another embodiment, the extract of *I. obliquus*, preferentially obtained in water under subcritical conditions, or the dermatological composition comprising same is used for preventing and/or reducing couperosis.

In an advantageous embodiment of the invention, the extract of *I. obliquus* will thus be included in a dermatological composition comprising at least one dermatologically acceptable excipient in a concentration of between 0.0001% and 20% by weight, preferentially between 0.001% and 5% by weight and more preferentially between 0.01% and 3% by weight relative to the total weight of the composition.

In a very advantageous embodiment of the invention, the extract is not used in combination with any extract of *Fomitopsis officinalis* and/or any extract of *Agaricus blazei*, advantageously not *A. blazei Muriill* and/or any extract of *Hericium erinaceum* for preventing and/or reducing irritations and/or itching. More advantageously, the composition according to the invention containing the extract of *I. obliquus* does not contain any extract of *F. officinalis* and/or any extract of *A. blazei*, and/or any extract of *H. erinaceum*. According to a more advantageous embodiment, the composition according to the invention does not contain any extract of *F. officinalis* or any extract of *A. blazei*, or any extract of *H. erinaceum*.

Examples referring to the description of the invention are presented below. These examples are given for illustrative purposes and shall in no way limit the scope of the invention. Each example has a general scope. The examples form an integral part of the present invention, and any feature appearing to be novel relative to any prior art, from the description taken in its entirety, including the examples, forms an integral part of the invention.

Unless otherwise indicated, the percentages are expressed on a weight/weight basis.

EXAMPLES

Example 1: Method for Obtaining an Extract of *I. obliquus*

Example 1a) An amount of 10% by weight of mycelium of the fungus *I. obliquus* relative to the total amount (weight) of fungus and of solvent was dissolved in water as sole solvent and macerated with stirring for a period of 1 hour at a temperature of 80° C. The extract was then decanted and centrifuged, and the supernatant was filtered (0.45 μm). The extract obtained is thus in liquid form.

Example 1b) An amount of 10% by weight of ground and dried mycelium of the fungus *I. obliquus* relative to the total amount (weight) of fungus and of solvent was dissolved in an ethanol/water mixture (70/30; v/v) and then macerated with stirring for a period of 1 hour at a temperature of 60° C. The extract obtained was decanted and centrifuged, and the supernatant obtained was filtered (0.45 μm). The ethanol was evaporated off and the extract was again filtered (0.45 μm). The extract obtained is thus in liquid form. Example 1c) An amount of 10% by weight of ground and dried mycelium of the fungus *I. obliquus* relative to the total amount (weight) of fungus and of solvent was extracted into water under subcritical conditions, at a temperature of 160° C. in an extraction column. The extract was then concentrated and filtered (0.45 μm). The extract obtained is thus in liquid form.

Example 1d) An amount of 10% by weight of ground and dried mycelium of the fungus *I. obliquus* relative to the total amount (weight) of fungus and of solvent was extracted into water under subcritical conditions, at a temperature of 160° C. in an extraction column. The extract was then concentrated and filtered (0.45 μm) and then dried and ground. The extract is in powder form.

Example 1e) The extract obtained as described in Example 1c) was diluted in glycerol to obtain a water-glycerol solution containing 80% by weight of glycerol.

Example 1f) The liquid extract obtained as described in Example 1a) was lyophilized. Example 1g) The liquid extract obtained as described in Example 1b) was lyophilized. Example 1h) An amount of 10% by weight of *sclerotium* of the fungus *I. obliquus* relative to the total amount (weight) of fungus and of solvent was dissolved in water as sole solvent and macerated with stirring for a period of 1 hour at a temperature of 80° C. The extract was then decanted and centrifuged, and the supernatant was filtered (0.45 μm). The extract obtained is thus in liquid form.

Example 1i) An amount of 10% by weight of ground and dried *sclerotium* of the fungus *I. obliquus* relative to the total amount (weight) of fungus and of solvent was dissolved in an ethanol/water mixture (70/30; v/v) and then macerated with stirring for a period of 1 hour at a temperature of 60° C. The extract obtained was decanted and centrifuged, and the supernatant obtained was filtered (0.45 µm). The ethanol was evaporated off and the extract was again filtered (0.45 µm). The extract obtained is thus in liquid form. Example 1j) An amount of 10% by weight of ground and dried *sclerotium* of the fungus *I. obliquus* relative to the total amount (weight) of fungus and of solvent was extracted into water under subcritical conditions, at a temperature of 160° C. in an extraction column. The extract was then concentrated and filtered (0.45 µm). The extract obtained is thus in liquid form.

Example 1k) An amount of 10% by weight of ground and dried *sclerotium* of the fungus *I. obliquus* relative to the total amount (weight) of fungus and of solvent was extracted into water under subcritical conditions, at a temperature of 160° C. in an extraction column. The extract was then concentrated and filtered (0.45 µm) and then dried and ground. The extract is in powder form.

Example 1l) The extract obtained as described in Example 1j) was diluted in glycerol to obtain a water-glycerol solution containing 80% by weight of glycerol.

Example 1m) The liquid extract obtained as described in Example 1h) was lyophilized. Example 1n) The liquid extract obtained as described in Example 1i) was lyophilized.

Example 2: Increase of the Expression of VE-Cadherin in Endothelial Cells in the Presence of an Extract of *I. obliquus*

Protocol: Normal endothelial cells (not originating from pathological tissue) were cultivated for 3 days in a medium containing FBS (foetal bovine serum). The growth medium was replaced with a medium for endothelial cells free of growth factor, and the cells were then incubated for 3 days in the presence of TNF-α (Tumour Necrosis Factor-α) (positive control) or with TNF-α supplemented with the extract of *I. obliquus* prepared according to Example 1d) or without any extract (control).

After the treatment, the cells were fixed with acetone for 10 minutes at −20° C. After washing with PBS buffer (phosphate saline), the sections were placed in a serum solution for 30 minutes. An anti-VE-cadherin primary antibody was incubated overnight at 4° C. After washes with PBS, a secondary antibody coupled to the fluorochrome Alexa 488 was applied for 45 minutes at room temperature (20° C.) and in darkness. The counter-stain Evans blue was applied after several washes for 5 minutes at room temperature. The observations were performed using a confocal microscope (TCS-SP2, Leica). Measurement of the mean area of the light of the micro-vessels was then performed using the images obtained. The statistical tests were performed via the Mann-Whitney test.

Figure 1:
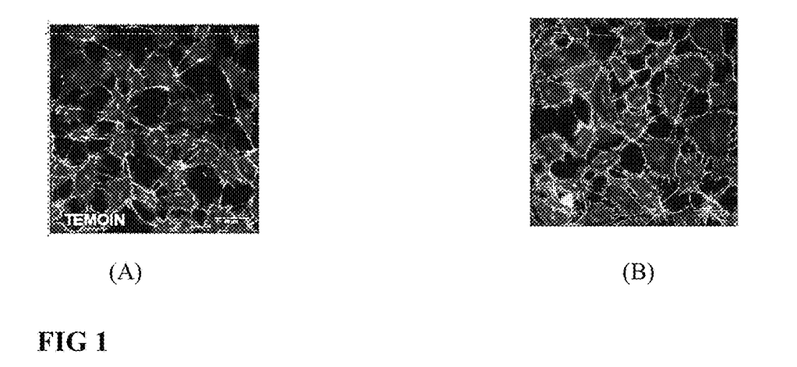
FIG. 1: Increase in the protein expression of VE-cadherin in endothelial cells in the presence of the extract according to the invention (A: control and B: Extract of *I. obliquus* (0.001% w/v medium))

Results and Conclusion:

The results are collated in Table 1 below and in FIG. 1.

TABLE 1

|  | Control | TNF-α | Extract of *I. obliquus* according to Example 1d + TNF-α |
|---|---|---|---|
| Mean | 424.37 | 108.43 | 507.45 |
| Standard deviation | 607.04 | 130.03 | 950.72 |
| SEM | 381.11 | 85.77 | 456.57 |
| Median | 240.81 | 59.40 | 237.25 |

The extract of *I. obliquus* made it possible to restore and to significantly increase the mean area of the light of the micro-vessels relative to the condition in the presence of TNF-α. FIG. 1 shows increased cohesion of the endothelial cells in the presence of the extract of *I. obliquus* according to the invention via increase of the protein expression of VE-cadherin, in comparison with the control. Thus, the extract of *I. obliquus* makes it possible to maintain and/or to increase the skin microcirculation. The same results are obtained using the extract according to Example 1k).

Example 3: Increase in Protein Expression of the Marker CD31 in a Model of Reconstructed Dermis Protocol:

Dermises composed of fibroblasts were obtained by inoculation and incubated in immersion for 21 days in DMEM (Dulbecco's Modified Eagle Medium) supplemented with 10% serum and vitamin C. The endothelial cells and the lymphatic cells were added and incubated in the presence of 10% serum and EGF (Epidermal Growth Factor). The sheets were superposed and incubated. Treatment with TNF-α (Tumour Necrosis Factor-α) (positive control) or with TNF-α supplemented with the extract of *I. obliquus* obtained according to Example 1d) (0.001% w/v) was performed for 7 days (n=4). Sections were made in paraffin in the reconstructed dermises and then subjected to labelling. The sections were deparaffinized and rehydrated, and were then recovered in citrate buffer. The sections were saturated by incubating with 2% bovine serum albumin (BSA). The sections were then incubated overnight with the anti-CD31 primary antibodies. After 5 washes, a secondary antibody coupled to the fluorochrome Alexa 488 was applied for 45 minutes in darkness. The observations were performed using a confocal microscope (Zeiss, LSM 700). Measurement of the mean area of the light of the micro-vessels was then performed using the images obtained. The statistical tests were performed via the Mann-Whitney test.

Figure 2:
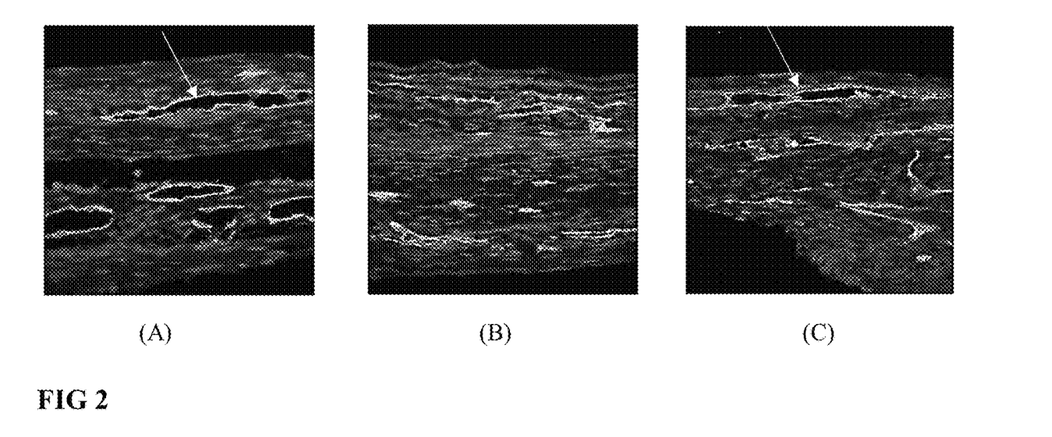
FIG. 2. Effect of an extract of *I. obliquus* on the sagging of endothelial structures in a model of reconstructed dermis subjected to a stress (marker CD31) (A: control, B: Stress (TNF-α) and C: TNF-α+extract of *I. obliquus*).

Results and Conclusion:

The results are collated in Table 2 below and in FIG. 2.

|  | Control | TNF-α | Extract of *I. obliquus* according to Example 1d + TNF-α |
|---|---|---|---|
| Mean | 865.76 | 93.62 | 530.20 |
| Standard deviation | 1473.41 | 154.83 | 1102.30 |
| SEM | 841.94 | 82.71 | 602.53 |
| Median | 391.33 | 46.65 | 138.60 |

TNF-α was used to mimic in vitro the effects of stress and is known to alter the organization and functioning of the microvascular structures of the skin. This is reflected by the presence of collapsed structures. They are referred to as sagging structures.

In the presence of the extract of *I. obliquus* prepared according to Example 1d), the microvascular structures of the skin were re-established (identical to the control). The extract according to the invention thus makes it possible to correct the effects of stress on the microvascular structures of the skin. Thus, the extract of *I. obliquus* makes it possible to maintain and/or to increase the skin microcirculation.

The same results are obtained using the extract according to Example 1k).

Example 4: Increase in Type IV Collagen Synthesis in the Presence of an Extract of *I. obliquus*

Example 4a) Keratinocytes

Protocol:

Keratinocytes not presenting any pathologies were cultivated at 37° C. in

KSFM specific culture medium (5% $CO_2$, 95% relative humidity) until confluence was reached and were then incubated with the extract of *I. obliquus* prepared according to Example 1d) or without the extract of *I. obliquus*, for a period of 48 hours. The culture media were removed and the cells were lysed with a lysis solution based on ammonium hydroxide. The wells were saturated for 30 minutes with BSA (bovine serum albumin) solution and then incubated for 1 hour with an anti-collagen IV antibody. After washing, the cells were incubated with the rabbit (goat anti-rabbit) secondary antibody for 1 hour. The media were removed and replaced with fluorescence revealing solution. The fluorescence was recorded at 340 exc/615 em nm.

The collagen IV concentration was deduced from a commercial collagen IV standard curve. The results were normalized relative to the amount of DNA contained in the cells (Picogreen kit).

Results:

TABLE 1

|  | MEAN (%) | SD |
| --- | --- | --- |
| Control | 100 | 6 |
| Extract of *I. obliquus* Ex. 1d) 1 × 10$^{-4}$ (w/v) | 241 | 12 |
| Extract of *I. obliquus* Ex. 1d) 1 × 10$^{-4}$ (w/v) | 226 | 16 |

Conclusion:

The extract of *I. obliquus* increased the expression of collagen IV in the keratinocytes by at least 100%, showing its capacity to increase the cohesion of the epidermal junctions. This extract thus makes it possible to increase the radiance of the complexion.

The same results are obtained using the extract according to Example 1k).

Example 4b) Fibroblasts

Protocol: Normal (non-pathological) fibroblasts were inoculated, cultivated for two days in specific culture medium (Normal Human Dermal Fibroblasts, Promocell) and then incubated for a period of 48 hours with or without the extract of *I. obliquus* prepared according to Example 1d). After cultivating, the cells were fixed with acetone for 10 minutes at –20° C., washed with phosphate-buffered saline (PBS) buffer, and then incubated in a serum solution for 30 minutes. An anti-collagen IV primary antibody was incubated for 2 hours at room temperature (20° C.). After washes with PBS, the secondary antibody coupled to Alexa 488 was applied for 45 minutes at room temperature (20° C.) and in darkness. The counter-stain Evans blue was applied after several washes for 5 minutes at room temperature (20° C.). The observations were performed using a confocal microscope (TCS-SP2, Leica).

Figure 3:
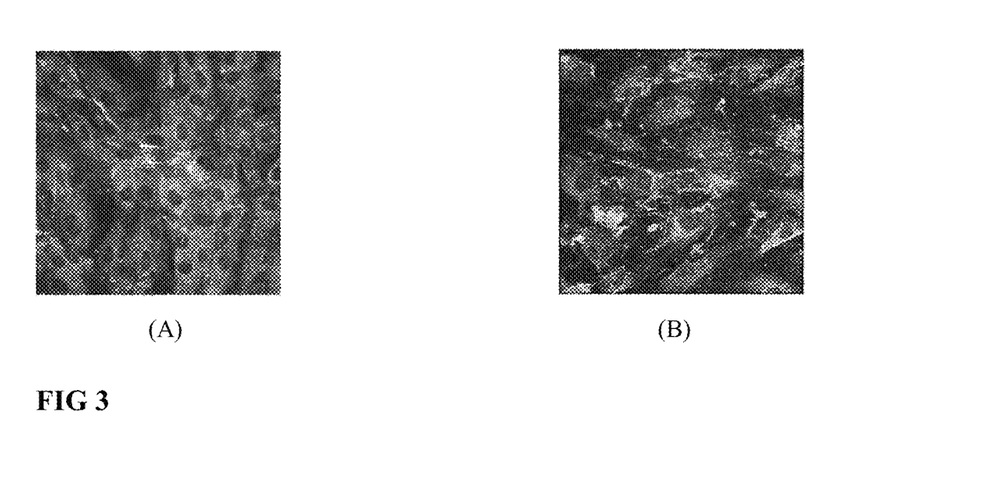
FIG. 3: Increase in the protein expression of type IV collagen in fibroblasts in the presence of the extract according to the invention (A: control and B: Extract of *I. obliquus* (0.001% w/v medium))

Results and Conclusion:

FIG. 3.

The extract of *I. obliquus* increased the protein expression of collagen IV in the fibroblasts, showing its capacity to increase the cohesion of the epidermal junctions. The extract according to the invention thus increases the radiance of the skin complexion.

The same results are obtained using the extract according to Example 1k).

Example 4c) Endothelial Cells

Protocol:

Normal endothelial cells (not originating from pathological tissue) were cultivated until confluence was reached at 37° C. (5% $CO_2$) in a culture medium specific for endothelial cells. The cells were incubated for 48 hours in the presence or absence of the extract of *I. obliquus* prepared according to Example 1d). After the treatment, the cells were fixed with acetone for 10 minutes at –20° C. After washing with PBS buffer, the slides were placed in a serum solution for 30 minutes. An anti-collagen IV primary antibody was incubated for 2 hours at room temperature (20° C.). After washing with PBS, a secondary antibody coupled to Alexa 488 was applied for 45 minutes at room temperature and in darkness. The counter-stain Evans blue was applied after several washes for 5 minutes at room temperature. The observations were performed using a confocal microscope (TCS-SP2, Leica).

Figure 4:
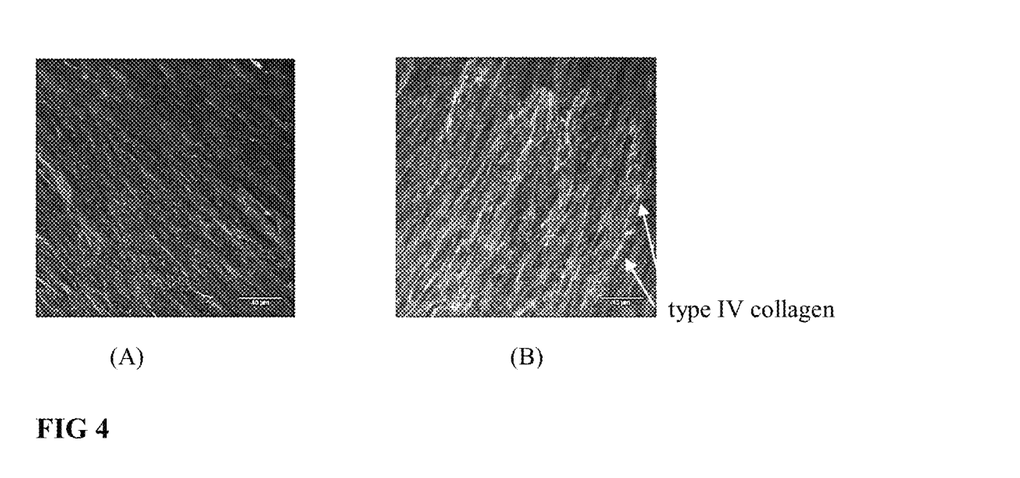
FIG. 4: Increase in the protein expression of type IV collagen in endothelial cells in the presence of the extract according to the invention (A: control and B: Extract of *I. obliquus* (0.001% w/v medium))

Results and Conclusion:

FIG. 4.

These results showed the capacity of the extract of *I. obliquus* to increase the protein expression of type IV collagen in the endothelial cells, and thus to increase their cohesion. The extract of *I. obliquus* according to the invention thus makes it possible to prevent the appearance of and/or to reduce bags and/or shadows in the area around the eyes.

The same results are obtained using the extract according to Example 1k).

Example 5: Increase in Protein Expression of the Marker HSP70 in the Presence of the Extract According to the Invention Protocol:

Fibroblasts were cultivated in FGM (Fibroblast Growth Medium) medium at a temperature of 37° C., under 5% $CO_2$ and 95% relative humidity, until confluence was reached. The cells were incubated with or without the extract of *I. obliquus* prepared according to Example 1d), for a period of 48 hours. The cells were rinsed with PBS (phosphate-buffered saline) buffer and then lysed. The lysates were collected and incubated for a period of 30 minutes with a rabbit anti-HSP70 primary antibody followed by a secondary antibody. The samples were eluted for 40 minutes to enable separation of the proteins as a function of their molecular weight by automated Western blotting. Detection of the protein HSP70 was performed after revelation by chemiluminescence. The amount of protein contained in the cell lysates was quantified using a commercial BCA (BiCinchoninic acid Assay) kit. The results were rationalized relative to the amount of protein and expressed as a percentage.

Results:

TABLE 2

| | MEAN (%) | SD |
|---|---|---|
| Control | 100.0 | 5.8 |
| Extract of *I. obliquus* Ex. 1d) 0.002% (w/v) | 133.8 | 7.7 |

Conclusion:

The extract of *I. obliquus* showed its effectiveness for increasing the protein expression of the marker HSP70, and thus its effectiveness in increasing the cohesion of the dermo-epidermal junctions, and thus makes it possible to maintain and/or increase the radiance of the skin complexion.

The same results are obtained using the extract according to Example 1k).

Example 6: In Vivo Measurement of the Increase in Radiance of the Complexion and Decrease in Ruddiness in the Presence of an Extract of *I. obliquus*

Protocol:

A clinical test was performed on a population of 33 women from 35 to 58 years old, presenting with facial ruddiness. The composition described in Example 9 containing 0.2% by weight of the extract of *I. obliquus* prepared according to Example 1c) relative to the total weight of the composition was applied to half of the face of the population of interest, twice a day for 7 and 28 days. The composition without the extract of *I. obliquus* replaced with water was applied as control to the other half-face of the population.

The intensity of the ruddiness and the luminous appearance of the skin were measured at times 0 (before the first application), T7 and T28 (7 and 28 days, respectively) using a chromameter by measuring the parameters a* and L*. A decrease in the parameter a* reflects a decrease in the intensity of the ruddiness. An increase in the parameter L* reflects an increase in the luminous appearance of the skin.

Results:

TABLE 3 in vivo Ruddiness results (parameter a*)

| | MEAN a* |
|---|---|
| Control T0 | 15.9 |
| Control T7 | 15.4 |
| Control T28 | 16 |
| Extract of *I. obliquus* 0.01% (w/v composition) T0 | 15.9 |
| Extract of *I. obliquus* 0.01% (w/v composition) T7 | 14.9* |
| Extract of *I. obliquus* 0.01% (w/v composition) T28 | 14.9** |

*$P < 0.05$;
**$P < 0.001$ (Student's test)

Conclusion:

A significant decrease in the intensity of the ruddiness of the half-faces was measured after 7 and 28 days of application of the composition comprising the extract of *I. obliquus* in comparison with the control, reflecting the capacity of the extract of *I. obliquus* for preventing and reducing ruddiness of the skin.

TABLE 4 in vivo Results of the luminous appearance of the skin (parameter L*) The same results are obtained using the extract according to Example 1k).

| | MEAN L* |
|---|---|
| Control T0 | 59.7 |
| Control T28 | 59.5 |
| Extract of *I. obliquus* 0.01% (w/v composition) T0 | 59.7 |
| Extract of *I. obliquus* 0.01% (w/v composition) T28 | 60.1* |

*$P < 0.001$ (Student's test)

Conclusion:

A significant increase in the parameter L*, and thus in the luminous appearance of the skin, was measured after 28 days of application of the composition comprising the extract of *I. obliquus*, in comparison with the control. The extract of *I. obliquus* is thus effective for increasing the radiance of the skin complexion.

The same results are obtained using the extract according to Example 1k).

Example 7: Increasing the Expression of Involucrin in the Presence of an Extract of *I. obliquus*

Protocol:

Normal (non-pathological) human keratinocytes were cultivated in the presence of 2% foetal calf serum and 0.03 mM calcium, at 37° C. (5% $CO_2$) for a period of 3 days, and then incubated with two increasing concentrations of the extract of *I. obliquus* or without the extract, for a further three days (extract of *I. obliquus* as prepared in Example 1d)). The protein involucrin was extracted and the amount thereof was measured via the ELISA technique. The results are expressed as a mean percentage versus the control (culture without addition of extract) (n=3).

Results:

TABLE 5

Involucrin

| | MEAN involucrin (%) |
|---|---|
| Control | 100 |
| Extract of *I. obliquus* Ex. 1d) 0.003% (w/v) | 207* |
| Extract of *I. obliquus* Ex. 1d) 0.01% (w/v) | 486* |

*$P < 0.05$ (Student's test)

Conclusion:

The extract showed its effectiveness for increasing the protein expression of involucrin in human keratinocytes and for differentiating them into corneocytes, making it possible to improve the cohesion of the epidermis, but also the barrier function of the skin.

The same results are obtained using the extract according to Example 1k).

Example 8: Reinforcement of the Cohesion of the Epidermis with an Extract of *I. obliquus*

Protocol:

"Normal" human keratinocytes, i.e. keratinocytes not presenting any pathologies, obtained from a healthy 59-year-old donor were cultivated for a period of 48 hours in the presence or absence (control) of two different final concentrations of the extract of *I. obliquus* prepared according to Example 1d), and the cell medium was then removed.

The cells were harvested and then lysed with a specific lysis buffer (CellLytic, Sigma) in order to perform the immunolocalization (Western blotting). The protein concentration was determined via the BCA method. The proteins were identified by capillary electrophoresis using anti-integrin β-1, anti-claudin-1 and anti-occludin primary antibodies and were then immunolocalized using a peroxidase-coupled conjugated secondary antibody. The results were quantified and expressed relative to the untreated control.

Results:

TABLE 6

| Integrin β-1 | |
| --- | --- |
|  | MEAN |
| Control | 100 |
| Extract of *I. obliquus* Ex. 1d) 0.01% (w/v) | 189* |

*$P < 0.01$ (Student's test)

TABLE 7

| Claudin-1 (C) and Occludin (O) | | |
| --- | --- | --- |
|  | MEAN C | MEAN O |
| Control | 100 | 100 |
| Extract of *I. obliquus* Ex. 1d) 0.001% (w/v) | 116* | 133** |
| Extract of *I. obliquus* Ex. 1d) 0.01% (w/v) | 120** | 162** |

*$P < 0.01$;
**$P < 0.001$ (Student's test)

Conclusion:

The extract of *I. obliquus* showed its capacity for stimulating the synthesis of integrin β-1, claudin-1 and occludin in skin keratinocytes. The extract is thus effective for increasing the cohesion of the epidermis, and can be used for protecting and comforting sensitive and/or intolerant and/or reactive skin.

The same results are obtained using the extract according to Example 1k).

Example 9) Formulation for the Face

| Formulation 9a) | |
| --- | --- |
| Water | Qs 100.00 |
| Cocoyl caprylate/caprate | 7.50 |
| Cetearyl alcohol | 4.00 |
| Propylheptyl caprylate | 2.50 |
| Propylene glycol, phenoxyethanol, chlorphenesin, methylparaben | 2.50 |
| Dipropylheptyl carbonate | 2.00 |
| Glycerol | 1.50 |
| Sucrose polystearate, cetyl palmitate | 1.00 |
| Extract of *I. obliquus* (Example 1c) | 0.20 |
| Sodium hydroxide | 0.32 |
| Carbomer | 0.20 |

| Formulation 9b) | |
| --- | --- |
| Water | Qs 100.00 |
| Cocoyl caprylate/caprate | 7.50 |
| Cetearyl alcohol | 4.00 |
| Propylheptyl caprylate | 2.50 |
| Propylene glycol, phenoxyethanol, chlorphenesin, methylparaben | 2.50 |
| Dipropylheptyl carbonate | 2.00 |
| Glycerol | 1.50 |
| Sucrose polystearate, cetyl palmitate | 1.00 |
| Extract of *I. obliquus* (Example 1j) | 0.20 |
| Sodium hydroxide | 0.32 |
| Carbomer | 0.20 |

The invention claimed is:

1. A cosmetic method for preventing the appearance of and/or reducing shadows and/or bags in the area around the eyes and/or for maintaining and/or increasing the skin microcirculation of an individual who requires or desires the same, comprising the following steps:
    (a) identifying on the individual an area of healthy skin and/or healthy mucous membranes for which it is desired to prevent the appearance of and/or reduce shadows and/or bags in the area around the eyes and/or to maintain and/or increase the skin microcirculation, and
    (b) applying to the area of healthy skin and/or healthy mucous membranes a composition comprising *Inonotus obliquus* extract in an effective amount for preventing the appearance of and/or reducing shadows and/or bags in the area around the eyes and/or for maintaining and/or increasing the skin microcirculation of this healthy skin and/or mucous membranes;
   wherein the extract is obtained by extraction into water under subcritical conditions and wherein the composition does not contain phytosterols and does not contain esters.

2. The method of claim 1, wherein the method is for protecting and/or comforting fragile and/or thin skin and/or mucous membranes and/or sensitive mucous membranes.

3. The method of claim 1, wherein the composition is a cosmetic composition comprising at least one cosmetically acceptable excipient, and the extract in a concentration of between 0.0001% and 20% by weight, relative to the total weight of the composition.

4. The cosmetic method of claim 1, wherein the application is a topical application.

5. The method of claim 4, wherein the area of healthy skin and/or healthy mucous membranes for which it is desired to prevent the appearance of and/or reduce shadows and/or bags in the area around the eyes and/or to maintain and/or increase the skin microcirculation is all or part of a human body selected from at least one of scalp, mucous membrane, leg, hand, thigh, stomach, neckline, neck, arm, torso, back, face, hip, waist, or area around the eyes.

6. The method of claim 1, wherein the extract is present in a cosmetic composition comprising at least one cosmetically acceptable excipient and the extract is in a concentration of between 0.001% and 5% by weight relative to the total weight of the composition.

7. The method of claim 5, wherein the area of healthy skin and/or healthy mucous membranes for which it is desired to prevent the appearance of and/or reduce shadows and/or bags in the area around the eyes and/or to maintain and/or increase the skin microcirculation is the neckline and/or the face.

8. The method of claim 5, wherein the area of healthy skin and/or healthy mucous membranes for which it is desired to prevent the appearance of and/or reduce shadows and/or bags in the area around the eyes and/or to maintain and/or increase the skin microcirculation is the area around the eyes.

* * * * *